US006103217A

United States Patent [19]
Charych

[11] Patent Number: 6,103,217
[45] Date of Patent: Aug. 15, 2000

[54] POLYMERIC ASSEMBLIES FOR SENSITIVE COLORIMETRIC ASSAYS

[75] Inventor: Deborah Charych, Albany, Calif.

[73] Assignee: The Regents of the University of California, Calif.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/901,220

[22] Filed: Jul. 28, 1997

Related U.S. Application Data

[63] Continuation-in-part of application No. 08/389,475, Feb. 13, 1995, abandoned, which is a continuation-in-part of application No. 08/289,384, Aug. 11, 1994, which is a continuation-in-part of application No. 08/328,237, Oct. 24, 1994, abandoned.
[60] Provisional application No. 60/022,942, Jul. 29, 1996.

[51] Int. Cl.[7] ............................. A61B 49/00; A01N 25/26; G01N 33/545; G01N 21/29
[52] U.S. Cl. ..................... 424/9.321; 424/1.21; 424/417; 436/518; 436/528; 436/531; 428/441; 428/462; 422/82.05; 422/82.09
[58] Field of Search ................................ 422/55, 57, 58, 422/82.05, 82.09; 427/2; 428/441, 462; 436/518, 528, 531, 829; 514/712.4; 424/1.21, 9.321, 417, 812, 420; 935/54

[56] References Cited

U.S. PATENT DOCUMENTS

| | | |
|---|---|---|
| 4,859,538 | 8/1989 | Ribi . |
| 5,268,305 | 12/1993 | Ribi et al. . |
| 5,415,999 | 5/1995 | Saul et al. . |
| 5,427,915 | 6/1995 | Ribi et al. . |
| 5,480,582 | 1/1996 | Pope . |
| 5,491,097 | 2/1996 | Ribi et al. . |
| 5,521,101 | 5/1996 | Saini et al. . |
| 5,571,568 | 11/1996 | Ribi et al. . |
| 5,618,735 | 4/1997 | Saul et al. . |
| 5,622,872 | 4/1997 | Ribi . |

OTHER PUBLICATIONS

Arisawa et al., "Quantitative characterization of enzymes absorbed on to Langmuir–Blodgett films and the application to a urea sensor," *Thin Solid Films* 210:443–445 (1992).
Berman et al., "Total Alignment of Calcite at Acidic Polydiacetylene Films: Cooperativity at the Organic–Inorganic Interface," *Science* 269:515–518 (1995).
Beswick et al., "Optical Detection of Toxic Gases Using Fluorescent Porphyrin Langmuir–Blodgett Films," *J. Colloid Interface Sci.* 124:146–155 (1988).
Chance et al., "Thermal effects on the optical properties of single crystals and solution–cast films of urethane substituted polydiacetylenes," *J. Chem. Phys.* 71:206–211 (1979).
Charych et al., "A 'litmus test' for molecular recognition using artificial membranes," *Chem. And Biol.* 3:113–120 (1996).
Furuki et al., "Hybrid gas detector of squarylium dye Langmuir–Blodgett film deposited on a quartz oscillator," *Thin Solid Films* 210:471 (1992).
Kaneko et al., "Absorption properties and structure changes caused by pre–annealing in polydiacetylene Langmuir–Blodgett films," *Thin Solid Films* 210:548–550 (1992).
Kingery–Wood et al., "The Agglutination of Erythrocytes by Influenza Virus is Strongly Inhibited by Liposomes Incorporating an Analog of Sialyl Gangliosides," *J. Am. Chem. Soc.* 114:7303–7305 (1992).
Mino et al., "Photoreactivity of 10,12–Pentacosadiynoic Acid Monolayers and Color Transitions of the Polymerized Monolayers on an Aqueous Subphase," *Langmuir* 8:594–598 (1992).
Miyasaka et al., "Amperometric Glucose Sensor with Oxidase Immobilized on $SnO_2$ Electrode via a Monolayer of a Photoreactive Nitrophenylazide Derivative," *Chem. Lett.*, p. 627–630 (1990).
Novotny et al., "Tribology of Langmuir–Blodgett Layers," *Langmuir* 5:485–489 (1989).
Okahata et al., "Preparations of Langmuir–Blodgett Films of Enzyme–Lipid Complexes: A Glucose Sensor Membrane," *Thin Solid Films* 180:65–72 (1989).
Ott et al., "Liposomes and influenza viruses as an in vitro model for membrane interactions II. Influence of vesicle size and preparation methods," *Eur. J. Pharm. Sci.* 6:333–341 (1994).
Reichert et al., "Polydiacetylene Liposomes Functionalized with Sialic Acid and Colorimetrically Detect Influenza Virus, " *J. Am. Chem. Soc.* 117:829–830 (1995).
Roberts, ed., *Langmuir–Blodgett Films;* Wiley, New York (1996); Reference could not be obtained at the present time. Applicant will provide copies of the title and copyright pages upon the Examiner's request.
Shibata, "Reversible Colour Phase Transitions and Annealing Properties of Langmuir–Blodgett Polydiacetylene Films," *Thin Solid Films* 179:433–437 (1989).
Swalen et al., "Molecular Monolayers and Films," *Langmuir* 3:932–950 (1987).
Tieke, "Langmuir–Blodgett Membranes for Separation and Sensing," *Adv. Mat.* 3:532–541 (1991).

(List continued on next page.)

*Primary Examiner*—Keith D. MacMillan
*Assistant Examiner*—P. Ponnaluri
*Attorney, Agent, or Firm*—Medlen & Carroll, LLP

[57] ABSTRACT

The presently claimed invention relates to polymeric assemblies which visibly change color in the presence of analyte. In particular, the presently claimed invention relates to liposomes comprising a plurality of lipid monomers, which comprises a polymerizable group, a hydrophilic head group and a hydrophobic tail group, and one or more ligands. Overall carbon chain length, and polymerizable group positioning on the monomer influence color change sensitivity to analyte concentrations.

39 Claims, 9 Drawing Sheets

OTHER PUBLICATIONS

Whitesides et al., "Wet Chemical Approaches to the Characterization of Organic Surfaces: Self–Assembled Monolayers, Wetting, and the Physical–Organic Chemistry of the Solid–Liquid Interface," *Langmuir* 6:87–96 (1990).

Spevak, "The Presentation of Biological Ligands on the Surface of Polymerized Monolayers and Liposomes," Ph.D. Dissertation, University of California at Berkeley (1993).

Lio et al., "Atomic force microscope study of chromatic transitions in polydiacetylene thin films," *J. Vac. Sci. Technol.* 14(2):1481–1486 (1996).

Leung et al., "Imaging of polydiacetylene on graphite by scanning tunneling microscopy," *J. Appl. Phys.* 69(4):2044–2047 (1991).

Rieke et al., "Spatially Resolved Mineral Deposition on Patterned Self–Assembled Monolayers," *Langmuir* 10:619–622 (1994).

Dagani, "Lipids and Minerals Form Novel Composite Microstructures," *Chem l & Eng. News,* 19–20 (1993).

Kessel and Granick, "Formation and Characterization of a Highly Ordered and Well–Anchored Alkylsilane Monolyaer on Mica by Self–Assembly," *Langmuir* 7:532–538 (1991).

Miyasaka et al., "Oriented Polypeptide Monolayers by Rapid Spontaneous Condensation of Amphiphilic Amino Acid Esters," *The Solid Films* 210/211:393–396 (1992).

Perez et al., "Toward Inorganic Monolayers Inserted in a Langmuir–Blodgett Matrix," *Thin Solid Films* 210/211:410–411 (1992).

Tanev and Pinnavaia, "Biomimetic Templating of Porous Lamellar Silicas by Vesicular Surfactant Assemblies," *Science* 271:1267–1269 (1996).

Yamanaka et al., "Solid Phase Immobilization of Optically Responsive Liposomes in Sol–gel Materials for Chemical and Biological Sensing," *Langmuir* 13:5049–5053 (1997).

Charych et al., Mat. Res. Soc. Symp. Proc., vol. 282, pp. 151–161, 1993.

Charych et al., Science., vol. 261, pp. 585–588, 1993.

Pons et al., Biochim. Biophy. Acta., vol. 693, pp. 461–465, 1982, 1993.

'PDA', 10,12 pentacosadiynoic acid
25 CARBONS TOTAL

'TRCDA', 10,12 tricosadynoic acid
23 CARBONS TOTAL

'ODA', 10,12 octadecadiynoic acid
18 CARBONS TOTAL

'TCDA', 5,7 tetracosadiynoic acid
24 CARBONS TOTAL

'DCDA', 5,7 docosadiynoic acid
22 CARBONS TOTAL

POLYMERIC ASSEMBLIES FOR SENSITIVE COLORIMETRIC ASSAYS

The present application is a continuation in part of prior-filed U.S. patent application Ser. No. 08/389,475 filed Feb. 13, 1995, now abandoned which is a continuation in part of U.S. patent application Ser. Nos. 08/289,384 filed Aug. 11, 1994, and 08/328,237 filed Oct. 24, 1994, now abandoned.

This application also claims priority to the provisional application Ser. No. 60/022,942 filed Jul. 29, 1996.

This invention was made with Government support under Contract No DE-AC03-76SF00098 between the U.S. Department of Energy and the University of California for the operation of Lawrence Berkeley Laboratory. The Government has certain rights in this invention.

BACKGROUND OF THE INVENTION

The present invention relates to a method for direct detection of analytes using color changes in liposomes which occur in response to selective binding of analytes to their surface.

Analytical Chemistry Analytical chemistry techniques have been used for many years to determine such medical parameters as hematocrit levels. While useful in their own right, analytical chemistry methods are of limited or no practical applicability to many biological parameters in which rapid and direct assessment would be valuable. Unless expensive and cumbersome gas or liquid chromatographic methods are used, measurement of biological analysis is difficult. Often, quantitative results are limited or not available. However, such techniques have been used for such basic chemical tests as creatinine assays.

Microbiological and Pathology Methods are another approach to medical-biological systems analysis by direct microscopic observation using various cell-staining and classic pathology techniques. Augmenting these capabilities have been well developed microbiological techniques, such as culturing, colony characterization, and observation of metabolic and nutrient limitations. Most of medical science have been developed using this basic arsenal of analytic techniques. While culturing and direct tissue observation techniques have served as the bulwark of medical detection processes for many years, they have considerable limitations. Pathological analysis of patient tissues to determine the development of a disease state and the identification of the causative pathogen generally requires an invasive procedure. On the other hand, culturing the pathogen from various body fluid or other samples is time consuming and expensive.

Immunoassays A breakthrough in medicine occurred with the development of immunoassay techniques. In these methods, an antibody is developed which will specifically bind to a target of interest. While costly in both their development and production, antibodies from animals allowed a very accurate analysis of a number of analytes which had previously been virtually inaccessible in both research and particularly clinical situations.

An important technical advancement in immunoassay was the development of monoclonal antibodies. Instead of subjecting an animal to an analyte and harvesting its whole range of antibodies, in this technique a single spleen cell of a sensitized animal is rendered immortal and multiplied many times. The resulting cell line is then cultured to produce a very specific and pure antibody product.

Because the antibody itself is a small molecule, it must be labeled in some way so that the binding event can be detected. This can be done with a dye, fluorescent, radioactive or other label. Conversely, if binding inhibition occurs between a known amount of introduced, labeled analyte and the material to be analyzed, the diminution of the signal will indicate the presence of test analyte. If the agglutination of the antibody particles is of sufficient volume and density, the formation of a precipitant can also serve to signal the presence of an analyte.

In recent years, the research and medical communities have come to rely heavily on immunoassay techniques to detect and quantify biological materials. While successful in many respects, the indirect nature of immunoassay methods as well as their dependence on antibody materials, results in a variety of complications, problems, and assay limitations. Briefly, the development and production of antibodies remain expensive, and these molecules are sensitive to environmental changes. Also, only those materials to which antibodies can be produced can be detected by these systems.

Langmuir-Blodgett Film Assays

The techniques of molecular self-assembly, such as that described by Swalen et al., (*Langmuir*, Vol. 3, page 932, 1987) as well as Langmuir-Blodgett (LB) deposition (Roberts, Ed. *Langmuir-Blodgett Films*, Wiley, New York, 1966) have been used for coating surfaces with a well-defined, quasi two-dimensional array of molecules. The initial use for this new advancement was for materials science applications such as wetting (Whitesides, et al., *Langmuir*, Vol. 6, p. 87, 1990) and friction (Novotny et al., *Langmuir* Vol. 5, p. 485, 1989). These bilayer films are also used as immobilizing supports for analytic reactions. Biosensors based on LB films can detect molecules of diagnostic significance such as glucose (Okahata, et al., *Thin Solid Films*, Vol. 180, p. 65, 1989) and urea (Arisawa, et al., *Thin Solid Films*, Vol. 210, p. 443, 1992). In these cases, classic analytical chemistry systems are immobilized on the films in order to improve the readout of the test results and otherwise simplify and improve the detection capabilities of the test procedure.

The detection of receptor-ligand interaction is generally accomplished by indirect assays such as the enzyme-linked immunosorbent and radio-labeled ligand assay. Although biotechnological functionalized films have led to elegant examples of molecular recognition at an interface, the problem of directly transducing the molecule recognition event into a measurable signal has remained a difficulty until the advent of the subject invention.

In the case of biosensor devices, detection is generally carried out by coupling the LB films to a secondary device such as an optical fiber (Beswick, *Journal Colloid Interface Science*, Vol. 124, p. 146, 1988), quartz oscillator (Furuki et al., *Thin Solid Films*, Vol. 210, p. 471, 1992), or electrode surfaces (Miyasaka, et al., *Chemical Letters*, p.627, 1990).

Some of the analyte bound films provide for fluorescent label, where the fluorescence or its quenched state indicate the occurrence of a binding event (Beswick, *Journal Colloid Interface Science*, Vol. 124, p. 146, 1988). In some cases, these detection materials have been embedded in the surface of the supporting bi-lipid layer (Tieke, *Advanced Materials*, Vol. 3, p. 532, 1991).

Polydiacetylene films are known to change color from blue to red with an increase in temperature or changes in pH due to conformational changes in the conjugated backbone (Mino, et al., *Langmuir*, Vol. 8, p. 594, 1992; Chance, et al., *Journal of Chemistry and Physics*, Vol. 71, p. 206, 1979; Shibutag, *Thin Solid Films*, Vol. 179, p. 433, 1989; Kaneko, et al., *Thin Solid Films*, Vol. 210, p. 548, 1992).

Functionalized Liposomes

Unpolymerized liposomes expressing sialic acid residues have been extensively used as model systems to study the interaction between influenza virus and cell surfaces (Ott, et al., *European Journal of Pharmacological Science,* Vol. 6, p 333, 1994). These liposomes are typically made of such lipid materials as cholesterol and egg phosphatidylcholine (Kingery-Wood, et al, *Journal of the American Chemical Society,* Vol. 114, p 7303, 1992).

The standard in the field is to progress with the polymerization procedure until the materials are fully red, indicating that the polymerization is complete.

While it has been a goal of the research community to exploit this characteristic in the detection of binding events, researchers have yet to develop a method using this phenomenon in practical applications. Ideally, such a development would include the potential for these materials to be in a liposome form.

SUMMARY OF THE INVENTION

The present invention provides several innovative chemical design approaches which provides high sensitivity of calorimetric films and liposomes, with excellent control of analyte concentration specificity. The inventor has discovered unexpectedly that controlling the placement of the polymerizable group in the monomer used as a precursor in colorimetric film and liposome production provides dramatically improved sensitivity. Careful selection of the placement of the polymerizable group can also provide a final color change reaction which is specific to an exact analyte concentration. Additionally, the overall carbon chain length of the monomer and the liposome size can also be designed in a manner which provides secondary means of controlling the sensitivity and analyte concentration specificity of the inventive improved colorimetric liposomes. The multiple means of controlling the sensitivity of responses provided by the present invention allows unprecedented control of the color change reaction.

The increase of sensitivity provided by the present invention for calorimetric films and liposomes opens up whole new areas of applications for calorimetric film and liposome technology. Dramatically extending the limits of this innovative technology, the present invention makes small materials such as biological toxins susceptible to detection using calorimetric liposomes. In the inventor's laboratory, cholera toxin has already been established as detectable using the innovations of the present invention. Small glycoproteins, such as Anti-DNP antibodies have also been detected, as well as large analytes such as toxigenic *E-coli* bacteria and viruses.

The innovations provided by the present invention also allow fine, incremental control of calorimetric film and liposome response to specific concentrations of analytes. By assembling films and liposomes from a mixture of monomers with differing polymerizable group placements, incremental sensitivity between the two homogeneous monomer constructs is achieved. Thus, the inventive method of engineering films and liposomes sensitive to a specific concentration of analyte allows customizing of these films and liposomes which will identify virtually any specific level of analyte.

Other methods of customizing sensitivity to specific analyte concentration have also been discovered by the inventor which can be employed in concert with control of carbon chain length to further augment customization of sensitivity ranges. For instance, larger sized liposomes, as well as those which form aggregates, have been found to be more sensitive in their color response to an analyte. Incorporating destabilizing materials into the films and liposomes can also serve to modify the level of concentration to which there will be a reaction to an analyte. Some such methods are described in U.S. patent application Ser. No. 08/609,312 filed Mar. 1st, 1996, to which the present inventor is a co-inventor.

It is an object of the invention to provide a calorimetric film or liposome assay for small analytes, large analytes with limited valance, or analytes at low concentrations.

It is a further object of the invention to provide a colorimetric film or liposome assay which will provide specific quantitation of an analyte.

The present inventive assay means and method provide for an improved direct colorimetric detection of a receptor-ligand interaction using novel polymeric films and liposomes. Using the inventive method of producing these original films and liposomes, a ligand or its derivative is incorporated into a polymeric assembly. Some of these aspects of the present invention are described in the inventor's published communication of which the inventor is one author, incorporated by reference herein, (Reichert et al, *J. Am Chem. Soc.,* Vol. 117, p 829, 1995).

The presence of an analyte which binds to the incorporated ligands can be detected by observing changes in the spectral characteristics of the inventive colorimetric films or liposomes. The calorimetric liposome of the present invention thus encompasses a molecular recognition site and a detection site, all within a single molecular assembly.

In one embodiment of the invention, chromatic polydiacetylene liposomes are produced, and placed in a liquid. The test sample is added. The color change which occurs indicates the presence of the analyte, and the degree of the color change allows a quantification of the analyte's concentration. Multiple wells of varying analyte concentration further refine the quantitation capacity of the present invention.

The inventor has prepared synthetic, polymerized liposomes that resemble the organization and functionalization of cell membranes and have employed them as simple colorimetric sensors. The liposomes can specifically bind to cholera and other pathogenic toxins, bacteria and virus, and in addition, report the binding event by undergoing a visible color change. In effect, these calorimetric liposomes mimic cell surface molecular recognition as well as signal transduction.

In order to impart both molecular recognition and detection functions to the liposomes, the inventor combined a known ligand-receptor interaction with the unique optical properties of certain polymers. The conjugated backbone of alternating double and triple bonds gives rise to intense absorption into the visible spectrum. In the case of polydiacetylenes in single crystals or Langmuir-Blodgett films, the inventive liposomes are known to undergo blue to red color transitions due to a variety of environmental perturbations including heat, mechanical stress, pH, and exposure to solvent.

In one embodiment of the invention, influenza virus particles are enveloped by a lipid bilayer to which the hemaglutinin (HA) lectin is anchored. HA binds to terminal alpha glycosides of sialic acid on cell-surface glyco-proteins and glycolipids, initiating cell infection by the virus. As described in the prior art section of the subject application, liposomes expressing sialic acid residues have been extensively used as model systems to study the interaction between influenza virus and cell surfaces. The polymerized liposomes of the subject invention, however, are composed of molecules that allow direct visualization of this specific interaction.

Advantages of the Invention

The present invention represents an advancement over the limitation of analytical chemistry techniques. Analytical chemistry techniques are the only assay system prior to the advent of the subject invention that allow direct detection. Unfortunately, analytical chemistry methods have limited applicability to many biological system's assay needs. Often, quantitative results from such methods are limited or not available. However, such techniques have been used for tests such as hematocrit analysis, and creatinine assays.

Analytical chemistry methods are virtually unavailable for most biological molecules due to the destruction of the analyte's characteristics during preparation and analysis steps, and the typically small amount of the analyte present in the test sample. For these reasons, the advent of immunoassay techniques were revolutionary in the biological sciences.

The present invention also represents an advancement beyond the limitations of immunoassay techniques. Many small biological molecules are notoriously difficult to assay in a direct manner due to the severe limitation of environmental ranges which they can tolerate without losing their specific characteristics. For these among other reasons, immunoassays have been heavily relied upon to assay these classes of materials. While successful in many respects, the indirect nature of immunoassay methods results in a variety of interference, complications, problems, and assay limitations and expense.

The requirement that an antibody be developed and produced for each possible target limits the efficacy of immunoassay methods in such applications as designer drug development and screening. Ironically, while allowing testing within a portion of biological environmental ranges, large glycoproteinaceous antibodies are often highly sensitive to degradation outside of a small testing parameter environmental range. Thus, the susceptibilities of antibodies to environmental challenges rigorously limit the environmental testing range available in these assay systems. In addition, immunoassays require multiple binding and washing steps and secondary reagents to visualize a binding event (i.e. "sandwich" assay). The inventive assay is one step.

A subtle disadvantage to immunoassay systems occurs in rapidly evolving pathogens such as the influenza virus. In such organisms, especially in the case of viruses, the external coat which is available for immune reactions constantly shifts in its antibody recognition elements. Thus, despite a full blown immunity response to an influenza strain, within months an individual can again develop flu, but from a pathogen with an external coat so modified that it is immunologically unrecognizable by the victims memory cells. This is the reason individuals can develop flu year after year.

The present invention enjoys the unique advantage over both immunoassay and analytical chemistry techniques of directly detecting biological analytes. In contrast to assays requiring binding to immunoglobulins, in one embodiment of the present invention, the host attachment site on the pathogen is exploited for recognition function. This site, generally in an immunologically inaccessible valley on the pathogen surface, is highly genetically conserved over time. The minimal variability of this site is necessary for the pathogen to maintain its infectivity. As a result, a single assay system of the present invention will provide effective assays for a panoply of influenza strains, many of which may be very newly evolved.

The inventive films and liposomes exploit the genetically conservative host binding site to identify the pathogen. Even in comparatively large parasites, the host binding site tends to be held constant over time throughout the generations of pathogens. Additionally, parasites are usually present in the body in a large number of diverse life stages. In well established parasites, the immune accessible sites often vary considerably from stage to stage, the advantage being that the host organism is unable to mount an immunological response with sufficient rapidity to avoid the entrenchment of the parasite. There are times when antibody is desired. In this case, the inventive assay is still superior to ELISA because it is one-step and direct.

The subject invention represents a dramatic advancement over both prior art direct chemical and immunoassay systems, achieving advantages which, prior to the present invention, were available exclusively in only one or the other of these analytic art methods. Much as the advent of immunoassay techniques revolutionized medical and research analytical capacities, the subject invention represents a critical advance in the analytical arts.

The present invention allows the advantages of both immunoassay and chemical analysis in a single system. The present invention enjoys the direct assay advantages of analytical chemistry methods, with many of the advantages inherent in such systems. The inventive assay technique also has a substantial environmental range of testing beyond that of immunoassays. This allows the accommodation of various analytes in their most advantageous environmental parameters. Additionally, the present invention allows rigorous, direct analysis to occur even in very narrow environmental ranges, previously unavailable with analytical chemistry techniques. The speed and simplicity of the color change indicator of the subject invention are its hallmark advantages. Large, expensive bulky equipment is not required. The assay can be carried out by a lay-person.

Analytes

One of the unique advantages of the subject invention is the wide range of target materials, binding events, and biochemical reactions amenable to analysis using the inventive techniques. Many of these materials previously could not be detected using a straightforward, practical assay. The present invention allows many of the advantages of immunoassay systems, without the complications of immunoglobulin generation or indirect analysis.

In general, the present invention requires no pre-analysis purification step. This feature of the subject invention is due to the high specificity of the ligands incorporated into the detecting polymeric assembly. Additionally, the inventive direct assay system avoids the expense, complications, and increased inaccuracies inherent in the indirect systems currently available.

The inventive liposomes can employ ligands and analytes which are stable or enjoy appropriate binding characteristics within a limited in vitro or environmental range of conditions. Within in vitro range conditions, the present invention is useful in that stringent limitations even within this narrow range of conditions can be met. This allows, for instance, three dimensional conformations of sensitive biochemicals and biomolecules to be maintained throughout the testing procedure, and can be used to detect infectious diseases such as respiratory diseases and sexually transmitted diseases. The inventive assays also can be applied to environmental monitoring, food pathogens, food processing packaging, manufacturing, and home health monitoring.

The present invention functions well even in carefully limited conditions. Thus, conditions such as pH, salinity, and temperature can be carefully controlled by feedback controls, titration and other techniques without interfering with the accuracy or sensitivity of the analysis.

Because of this wide experimental range advantage of the present invention, intact cells or sensitive sub-cellular inclusions can be assayed without disturbing their structural integrity. The color change when the inventive assemblies bind to a surface will pinpoint the location of an analyte, such as in a tissue sample.

Subtle cellular development stages can be monitored by the present invention, such as the various stages of malaria infection. Additionally, the association between various factors can be tested or monitored even during the interaction process using the method of the subject invention.

A structural linker of sufficient length and conformability aids in allowing binding of multiple sites on the analyte even when they are conformationally separated on a curved surface. As a result of these special features, the present invention can detect many ligands previously unsuitable for assay evaluation.

The main criteria for effective indication of the presence of analyte is that the surface of the liposomes be sufficiently perturbed to produce the requisite spectral change. Binding the analyte to an immobilizing particle will serve this purpose, as it concentrates the analyte in a small area, and further provides a three-dimensional aspect over a relatively large area to even a small analyte.

A large variety of ligands can be employed in the subject invention, allowing great flexibility in detecting a test target. Ligand selection can be based on the most advantageous binding and steric characteristics, rather than compromising these factors to accommodate the test system. Thus, the most advantageous ligand can be selected based on such factors as hydrophobicity and hydrophilicity, size, position of binding site, and conflicting affinities. Ligands which can be employed in the subject invention can include carbohydrates, peptides, nucleotides, heterocyclic compounds, and other organic molecules.

In cases where specific binding ligands are not known, specific antibodies can be attached to the liposome surface or the (Fab)2 fragments can be attached. Any antibodies raised against the analyte can be used for bio-recognition.

The rigor and outstanding advantages of the inventive assay system allows the direct and rapid detection and quantitative evaluation of materials which have been previously unachievable because of the limitations of the prior art methods.

The inventive liposomes and assay method can also assay very small biological or other molecules for which antibodies can not be developed. These target materials can include organic solvents or pollutants present at extremely low levels. There are special opportunities made available by the advances achieved by the subject inventors for drug screening in both forensic and clinical applications. Inhibition techniques applied to the subject invention can allow the testing of materials which are of a tiny size or have a small number or single valency.

While applicant is not bound there by, it is hypothesized by the inventors that the unexpected spectral signal achieved by the present invention is due to a physical perturbation of the liposomes which occurs as a result of the binding event. It is the case that multivalent materials, such as viruses and cell membrane fragments, can be very easily detected using the subject inventive method. Thus, multivalent materials generally elicit a particularly strong response in the subject system. This may be the case because of conformational changes introduced into the lipid bi-layer as a result of binding causing physical reconfiguration of structure. In addition, materials which can intercalate into the lipid bilayer also elicit a strong response.

Signal Observation

Various spectral changes to the inventive bi-layer films and liposome can be used to detect the presence or absence of the target material. Means of amplifying the spectral signal well known in the art, such as scintillators, can also be employed when low levels of analyte are present. Because of the colorimetric nature of the signal, there are many opportunities for automating the read out of the present inventive assay system.

In one particular embodiment of the present invention, a blue to pink color shift can be observed simply by visual observation by the testing technician. Because of the simplicity of the observation, this function can easily be accomplished by an untrained observer such as an at-home user. Alternatively, spectral test equipment well known in the art can be employed to determine a change in spectral qualities beyond the limits of simple visual observation, including optical density to a particular illuminating light wavelength.

The subject liposomes can also be optimized in assays by binding them to any one of a number of immobilizing materials and objects. Bonding to sephedex beads, for instance, would allow flow-through and washes to be possible during the assay procedures. The inventive assemblies could even be embedded in a gel, with the analyte diffusing through it, possibly with an electrical gradient.

DETAILED DESCRIPTION OF THE INVENTION

Figure 1:
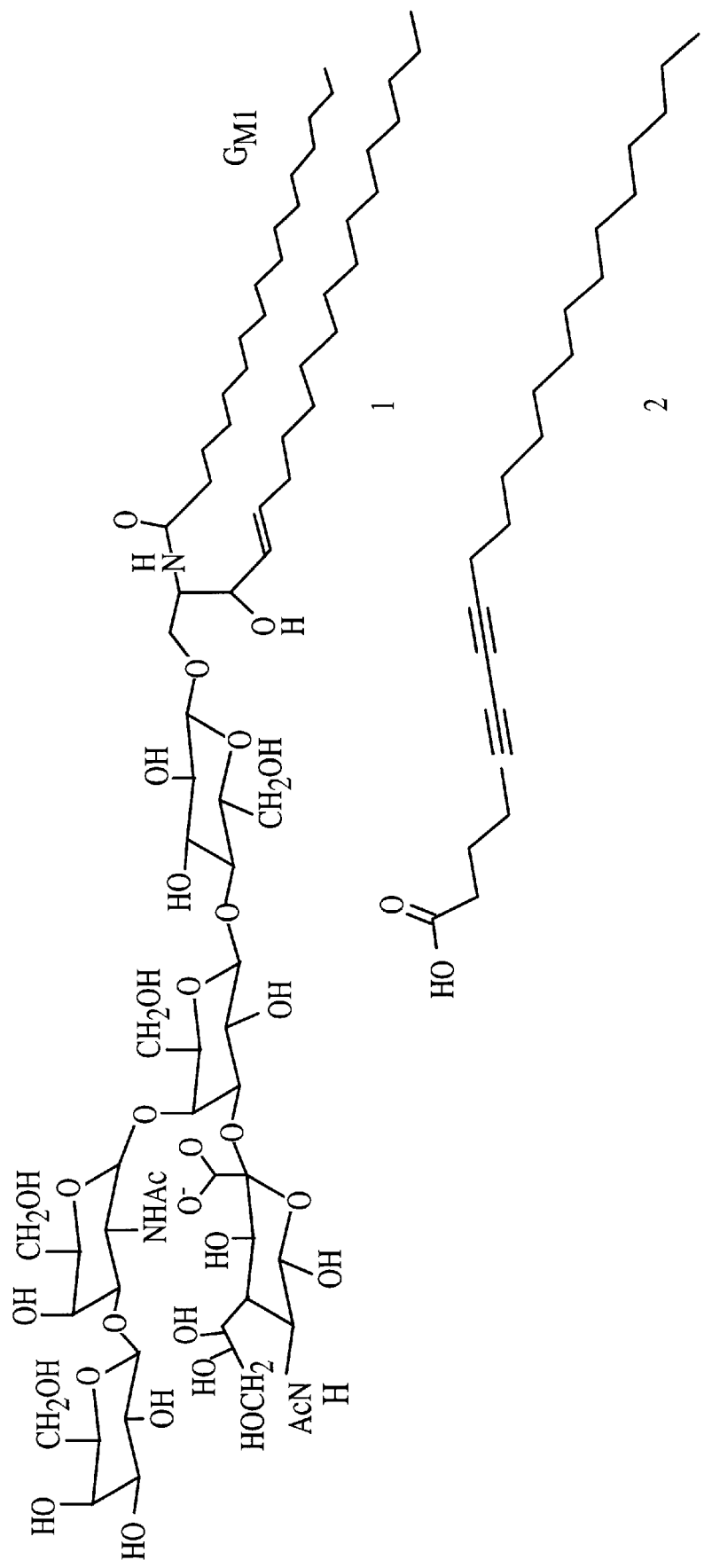
FIG. 1 is a chemical structural representation of cholera toxin $G_{M1}$ and PDA monomer 5,7-Docosadiynoic acid.

The present invention provides several innovative chemical design methods to increase and control the sensitivity of colorimetric liposomes assays previously developed by present inventor along with other researchers, as set forth in U.S. parent application Ser. No. 08/389,475, filed Feb. 13, 1995 now abandoned. It has been found unexpectedly that by positioning the polymerizable group, such as the diacetylene group on the precursor monomer closer or farther from the head group end of the monomer, the final liposomes product will have an increased or decreased color change sensitivity to analyte concentrations. This allows the engineering of liposomes which react to lower valency analytes or only at a specific level of analyte concentration. Overall carbon chain length, and liposome size also influence sensitivity to analyte concentration level, and can be used to augment and extend the sensitivity control provided by the diacetylene group positioning.

The dramatically increased sensitivity provided by the invention allows for the first time, the use of calorimetric liposome assays to detect small clinically and toxicological significant analytes such as cholera toxin. Additionally, the present invention provides for the detection of large, low valence analytes, weak binding analytes, and analytes present at very low concentrations.

By assembling liposomes from a mixture of monomers with differing polymerizable group placement, incremental sensitivity between the two homogeneous monomeric constructs is achieved. Thus, the inventive method of engineering liposomes with a color change reaction limited to a specific concentration of analyte allows customizing of liposomes which will react to virtually any incremental level of analyte concentration.

The other methods of customizing sensitivity discovered by the inventor can be employed in concert with control of polymerizable group placement to further augment customization of analyte concentration sensitivity. Another factor in providing control of sensitivity is regulating the overall carbon number in the monomer.

By providing a series of analytical units of progressive sensitivities, quantitation of an analyte can be direct and very quickly achieved. By example, a series of analytical wells or films of incremental sensitivity can be provided in the same unit. When a single sample to be analyzed is washed over the group, the presence of the analyte can be quantitated. The series of wells which displayed a positive reaction provide a continuum indicating the concentration of analyte contained in the sample, while providing the quality assurance of multiple reactions. Differences in color hue can then be used to fine-tune the quantitation or provide a secondary method of assuring selectivity based on the pattern produced.

This multiple well method provides the quality control advantage of providing both positive and negative controls. This approach would avoid problems should any single well malfunction, potentially providing inaccurate information.

The present invention is particularly suitable for detecting analytes which were undetectable by the previous colorimetric liposome detection methods because of their small size. Various specific pathogen toxins are good candidates for detection using the present invention.

A case in point is the cholera toxin from Vibriocholerae, which is about 38,000 MW. Specifics as to the protocol used to obtain the detection of this small molecule are set forth below as Example 1. Other toxins, such as pertussis toxin or entero toxins from enteropathic bacteria such as E. coli are also detectable using the present invention.

Using the approach of the present invention, a great variety of small molecules will be susceptible to detection using colorimetric liposomes. By example, the inventor has detected anti-DNP antibody using the inventive technology. This glycoprotein has a molecular weight of 150,000. Other small proteins and other small analytes are equally detectable using the present invention.

Molecular recognition sites for specific analytes are excellent sources of ligands for the inventive liposomes. Molecular recognition sites on cell membranes serve as the main communication channels between the inside of a cell and its surroundings. Upon receptor binding, cellular messages such as ion channel opening or activation of enzymes are triggered. The inventive liposomes serve as artificial cell membranes made from conjugated lipid polymers such as polydiacetylene which can on a simple level, mimic membrane processes of molecular recognition and signal transduction. The surface of a cell membrane is a mosaic of highly specific molecular recognition receptor sites. When specific ligand binding occurs at these sites, the binding event is often transduced into a cellular message. Cell membrane recognition sites may trigger, for example, the opening of ion channels or the activation of intracellular enzymes. From the materials science point of view, the cell membrane may be considered a completely self-contained biosensing system wherein molecular recognition is directly linked to signal transduction.

Analytes include, but are not limited to viral and bacterial pathogens, enzymes, drugs, toxins, viruses, proteins, hormones, bacterial enzymes, pathogenic toxins, cholera toxin, pertussis toxin, enterotoxin, toxin A, *Candida albicans,* anti-DNP, IgG antibody, Streptococcus, GABA binding protein, dopamine D2 receptor, phospholipase A2 enzyme, serotonin receptors, *Neisseria gonorrhoea, E. coli, Bacillus anthracis,* Chlamydia, vaccinia, rabies, Epstein Barr virus, polio virus, neutrophils, coronavirus, influenza virus, encephalomyelitis viruses, Sendai virus, mumps, Newcastle disease virus, myxovirus and encephalomyocarditis viruses, as well as meningitis, malaria, and HIV analytes.

The inventor has been interested in the design of synthetic membranes that attempt to mimic, on a very simple level, the complex molecular choreography of cell membranes. The simplified constructs allow the study of fundamental receptor-ligand interactions and, in a more practical sense, the application of receptor-ligand binding to biosensor design.

The synthetic membranes of the present inventive liposomes are organized supramolecular structures that resemble natural cell surfaces at the interfacial region but possess a chromophoric conjugated polymer at its interior. The latter part serves as an optical "transducer" of molecular recognition events occurring at the interface. Signaling occurs by a simple color change of the chromophoric unit from blue to red.

The inventors and other fellow researchers demonstrated that polydiacetylene (PDA) thin films and liposomes functionalized with sialic acid molecular recognition groups can bind and calorimetrically detect influenza virus (Reichert, et al *J. Am. Chem. Soc.,* Vol 117, p 829, 1995; and Berman, *Science* V. 269, p 515, 1995). The multivalent nature of viral binding at the interface triggered large conformational changes in the polymer side chains followed by disruption of conjugation in the chromophoric polymer backbone. The result is a visible color change from blue to red, similar to color changes previously observed in PDA induced by heat (thermochromism) and mechanical stress (mechanochromism).

For the viral binding study, the ligand molecule for the biotarget was a synthetic diacetylenic lipid compound derivatized with the binding ligand. The ligand-lipid could be cross-linked with the remaining diacetylene groups forming the conjugated polymer backbone. More recently, the inventor and other researchers showed that naturally derived lipophilic molecules can be incorporated into polydiacetylene Langmuir-Blodgett films. (Charych, *Chem. Biol.* V 3, p 113, 1996). The present invention demonstrates that these molecules can also be formed into liposomes when mixed with a polymerizable monomer lipid.

Gangliosides are a complex subclass of sphingolipids that are derivatives of ceramide. The large polar head is made up of several carbohydrate units. The membranes of the human nervous system contain at least 15 different gangliosides of which little is known about their function. However, in addition to its natural role in animal cells, the ganglioside $G_{M1}$, as shown in FIG. 1, is the point of attachment of cholera toxin as it attacks the cell. This interaction provides a useful model to demonstrate molecular recognition between the protein toxin and the lipid-polymer matrix.

Molecular recognition sites for specific analytes are excellent sources of ligands for the inventive liposomes.

Polymerizable Group Placement in Monomer Carbon Chain The carbon chain length positioning the head group a specific distance from the polymer backbone in the final polymerized liposome is dependent on the position of the polymerizable group in the unassembled monomer. It has been discovered by the inventor that, in the case of diacetylene liposomes a diacetylene group positioned from between the 18–20 positions to the 3–5 position in the monomers will produce progressively more sensitive liposomes. Liposomes produced from monomers with the diacetylene groups from the 10–12 position to the 4–6 position provides particularly efficient control of sensitivity. Diacetylene groups positioned in about the 5–7 position are preferred, such as in cholera toxin detection. The production protocol for the monomer determines at which position the diacetylene group will be placed in the final monomer product.

Total Carbon Chain Length The total carbon chain length in the unassembled monomer will also influence the level of sensitivity of the liposome product, although to a lesser extent than the position of the polymerizable group in the monomer carbon chain. The shorter chain length typically provides for greater sensitivity. The monomers which are useful in construction of the inventive colorimetric liposomes can range from between $C_{12}$ to $C_{25}$ in length. A preferred range of monomer carbon chain length in the present invention is $C_{20}$ to $C_{23}$. The most preferred carbon length for monomers in the present invention is $C_{22}$.

The synergistic influence of monomer chain lengths and positioning of the polymerizable group on the chain has been concretely demonstrated in experimental work completed by the inventor. It was shown that in the case of 10,12 derivatives, that the $C_{23}$ chain provides final calorimetric liposomes product which changes color at a lower analyte level than those produced from monomers with a $C_{25}$ chain. In the case of 5,7 derivatives, the $C_{22}$ length chain provides a greater sensitivity than the $C_{24}$ length chain.

Analytical Devices The present invention provides a special opportunity to provide an instant and continuous reading of the level of analyte in a sample. This capacity of the present invention has important applications in monitoring materials present in a feed stream or an environmental area of concern. As an example, personal safety of waste management and cleanup workers is an important factor at various facilities, and this technologic advancement would have special applications in such situations.

A good method of displaying incremental levels of analyte using the present invention is by a series of wells which will react at different titrations of analyte. The series of wells which displayed a positive reaction provide a continuum to indicate the concentration of analyte contained in the sample, while providing the quality assurance of multiple reactions. Differences in color hue can then be used to fine-tune the quantitation. The multiple sequential sensitivity well method provides the quality control advantage of providing both positive and negative controls. This approach would avoid problems with any single well providing inaccurate information.

An alternative to the multiple method is to provide liposomes of incrementally advancing sensitivities in an immobilized state. This approach provides a continuous display of analyte concentration. Column or dipstick devices are natural applications for this embodiment of the inventive technology. A wide range of production methods are also applicable to the present invention. For instance, providing layers of immobilizing gels containing liposomes of ever increasing sensitivity would allow a layered cake production. Careful slicing would provide inexpensive production of single strip units capable of detecting multiple levels of analyte.

General Liposome The inventive colorimetric liposomes allow for the direct detection of the presence of a wide range of analytes by changes in color. The results can be read by an untrained observer, and the test can be conducted in ambient conditions. Very mild testing conditions are possible, which allows the detection of small biomolecules in a near natural state, providing information as to their interactions and avoiding the risk of modification or degradation of the analyte.

Lipid Ordering Groups The lipids appear to be important in structurally ordering the three-dimensional liposomes so that binding of the analyte produces a detectable color change. The inventor hypothesizes that a structuring effect of the ordering groups serves to appropriately stabilize the physical structure of the three-dimensional liposomes to facilitate color stability and polymerization. In turn, the binding of the analyte to the molecular recognition ligand groups then causes sufficient steric perturbation or stress of the structure to result in a color change. It may be that the stability and relative rigidity engendered by the ordering lipids so unites the bilayer surface, that a steric change in one area triggers a larger effect in the surface of the assemblies as a whole. It is further hypothesized that the shortened chain lengths of the present invention decrease the stability of the structure thus providing a reaction to low levels of analyte.

It is not certain which of the many results of binding result in the observed spectral changes. Most likely the changes are due to stresses induced by binding which changes the effective conjugation length of the polymer backbone. The inventive three-dimensional structures are highly color sensitive to a number of environmental parameters, such as heat, and these factors may be a component of the observed phenomena as well. However, the applicant is not bound to any of the above hypothesis which are simply attempts to explain the demonstrated effective assay method of the subject invention.

Previous studies have suggested that color transitions in polydiacetylenes arise from changes in the effective conjugation length of the polydiacetylene backbone and that the electronic structure of the polymer backbone is strongly coupled to side chain conformation. The inventor can only speculate at this point that specific analyte-liposome interactions may serve to alter side chain conformation, reducing the effective conjugation length of the enzyme backbone. Indeed, theoretical calculations suggest that very slight around the C—C bond of the polymer backbone decrease the $\pi$ electron delocalization.

Head Group Materials for use as head groups in the present invention include —CH₂OH, —CH₂OCONHPh, —CH₂OCONHEt, —CH₂CH(Et)OCONHPh, —(CH₂)₉OH, —CH₂OCOPh, —CH₂OCONHMe, —CH₂OTs, —CH(OH)Me,
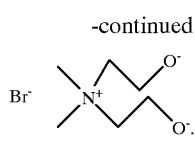
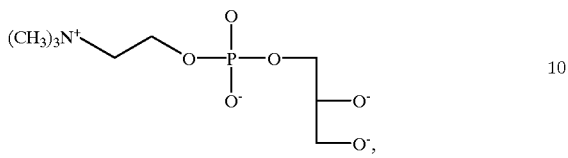
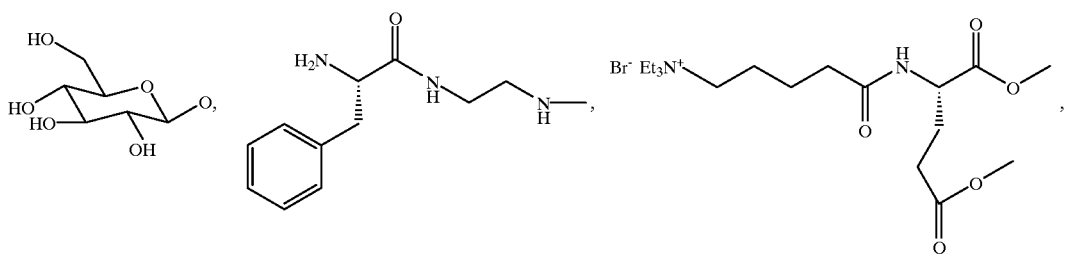
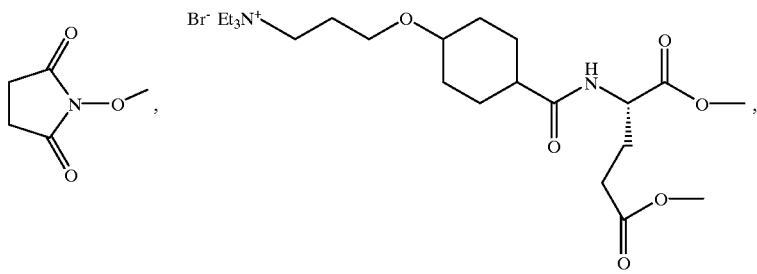
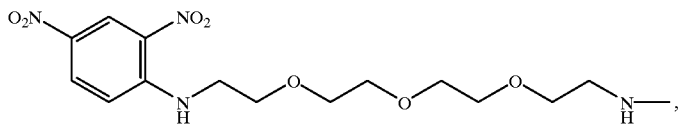
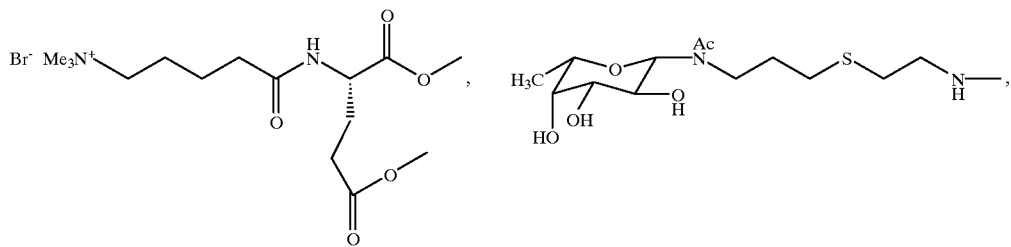
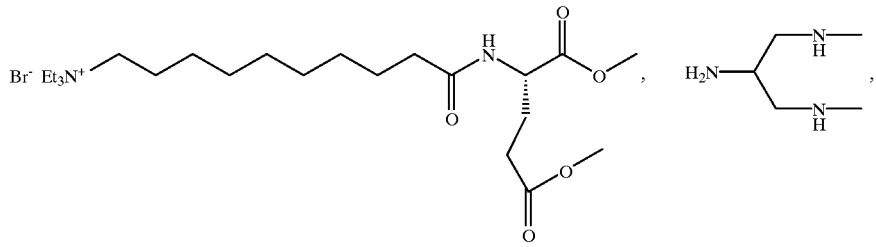

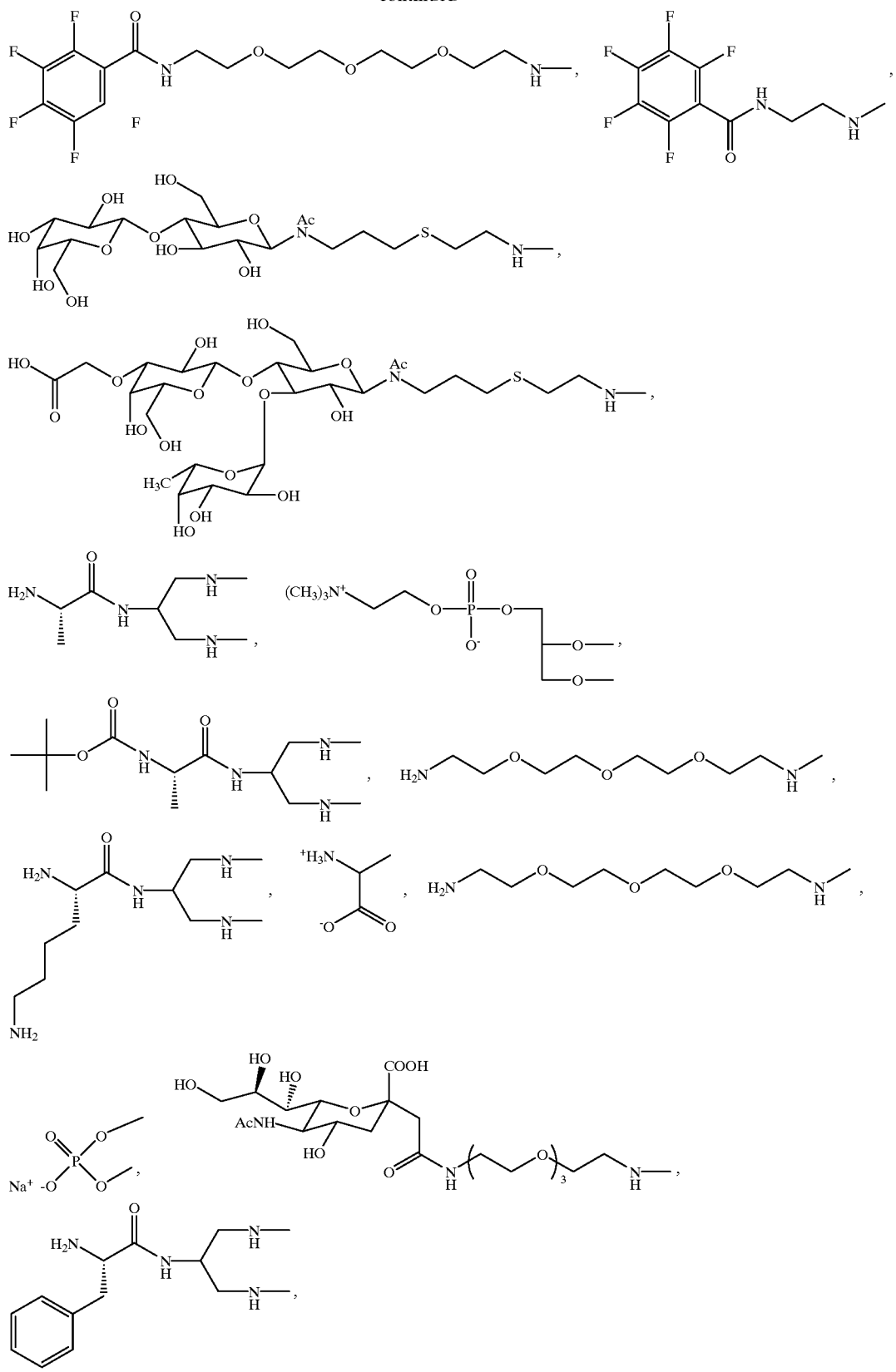

—CH$_2$OCOR$_2$, wherein R$_2$ n-C$_{17}$H$_{35}$, Ph, PhO, or
—OSO$_2$R$_2$, wherein R$_2$ is Ph, p-MeC$_6$H$_4$, p-FC$_6$H$_4$, p-ClC$_6$H$_4$, pBrC$_6$H$_4$, p-MeOC$_6$H$_4$, m-CF$_3$C$_6$H$_4$, 2-C$_{10}$H$_7$, or Me—
CO$_2$M, wherein M is K,HNa, or Ba/2.

The preferred materials which can be employed as head groups in the present invention are:

—CH$_2$OCONHR$_2$ or —CH$_2$CONHR$_2$ where R$_2$ is Et, n-Bu, n-C$_6$H$_{13}$, n-C$_8$H$_{17}$, n C$_{12}$H$_{25}$, cyclo C$_6$H$_{11}$, Ph, p-MeC$_6$H$_4$, m-MeC$_6$H$_4$, o-ClC$_6$H$_4$, m-ClC$_6$H$_4$, p-ClC$_6$H$_4$, o-MeOC$_6$H$_4$, 3-Thienyl, Me, Et, Ph, 1-C$_{10}$H$_7$, Et, Ph, EtOCOCH$_2$, BuOCOCH$_2$, Me, Et, i-Pr, n-C$_6$H$_{13}$, EtOCOCH$_2$, BuOCOCH$_2$, Ph, 2,4(NO$_2$)$_2$ C$_6$H$_3$OCH$_2$, or CH$_2$CH$_2$OH.

The most preferred head groups are taken from —CH$_2$COX, where X is OH, MeO or any salt thereof.

Ligand Group The ligand group of the present invention can be of a wide variety of materials. The main criteria is that the ligand have an affinity for the analyte of choice. The ligand may be of a broad range, such as when a class of materials is to be assayed. Appropriate ligands include peptides, carbohydrates, nucleic acids or any organic molecules which bind to receptors. For instance, all influenza strains share binding sites to a host receptor molecule. Thus, this molecule can successfully be employed to screen for all influenza strains, including those which have not yet been characterized.

Ligands include, but are not limited to oligosaccharides, mannose sugar, pepstatin, dinitrophenol, biotoxin, GABA, dopamine, spiperon, phospholipid substrate, serotonin, galactose, monoclonal antibodies, epidermal growth factor, acetylcholine, complement receptor, beta-adrenergic receptor, reovirus receptor, tetrasaccharide, sialic acid, sialic acid derivatives, transmembrane receptors, CD4, CD26, vasoactive intestinal peptide, and peptide T. It is intended that ligands include derivatives and analogues capable of associating with analytes which include, but are not limited to vaccinia, rabies, Epstein Barr virus, polio virus, neutrophils, coronavirus, influenza virus, encephalomyelitis virus, Chlamydia, Sendai virus, mumps, Newcastle disease virus, myxovirus and encephalomyocarditis virus, as well as meningitis, malaria, and HIV analytes.

Ligands can also be used in the present invention when they function as competitive binders to the analyte. For instance, a pathogen could be introduced with a test material which is to be the presence of receptor molecule. In absence of this molecule, the pathogen will bind to the three-dimensional polymeric structure and produce a color. To the degree that the pathogen surface is bound to the receptor molecule introduced in the test material, the binding will be diminished. In this way, the presence of receptor molecule can be detected and quantified.

Receptor-Binding Molecules The use of sialic acid derivatives in one preferred embodiment described in the examples below is an example of the use of receptor-binding molecules in this capacity. Receptor-binding molecules are materials on the surface of a host cell to which a pathogen attaches itself as a prelude to the infective event. Selecting these molecules at the ligand group in the present invention has many advantages over other receptor molecules. The recognition sites for these molecules tend to be highly genetically conserved in the pathogen because of its obvious criticality to survival. Therefore, different strains of the same pathogen will generally not produce a false negative when such molecules are selected as the ligand group in the subject invention. Also, receptor molecules tend to be smaller and less complex, and often less hydrophobic, then antibodies to the same analyte.

An increasing number of receptor molecules are being recognized, identified, isolated, and synthesized for a large number of pathogens. Many have been improved for use in various analytic and treatment systems. An example of this trend in research is the sialic acid derivative used in the example below of the subject invention. Examples of the receptors for a number of pathogens are provided in the application as Table 1. All of these, as well as many more, could be exploited by the method of the subject invention.

Lipid Polymerization Groups Many different polymerizing groups have been incorporated into lipids and are shown to be effective in monolayer polymerizations. Such moieties include: acetylenes, diacetylenes, alkenes, thiophenes, imides, acrylamides, methacrylates, vinylether, malic anhydride, urethanes, allylamines, siloxanes or vinylpyridinium etc. Lipids containing these groups can be made into homopolymers or mixed polymers. The preferred group for use in this invention is the diacetylene due to its unique optical properties in the polymerized form: Polydiacetylene. However, other polymerizing groups could be used when they provide an observable change in properties upon a binding event.

Detection of Cholera Toxin

Cholera toxin is an enterotoxin of the Gram-negative bacterium *Vibrio cholerae* that causes potentially lethal diarrheal disease in man. The cholera-$G_{M1}$ interaction is well-characterized and the $G_{M1}$ lipid can be easily incorporated into liposomes. Cholera toxin is composed of two subunits: A (27 kDa) and B (11.6 kDa) with the stoichiometry AB$_5$. The B components bind specifically to $G_{M1}$ gangliosides on cell surfaces, ultimately leading to translocation of the A1 fragment through the membrane. Previous studies have shown that cholera toxin could be recognized by $G_{M1}$-containing supported lipid membranes and polymerized Langmuir-Blodgett films containing $G_{M1}$ and a carbohydrate "promotor" lipid. The ganglioside $G_{M1}$ was mixed at 5 mol % with the diacetylene "matrix lipid" monomers, 2. Liposomes were prepared using the probe sonication method and polymerized by UV irradiation (254 nm). The solid-state polymerization proceeds as a 1,4 addition controlled by the packing of the monomers.

Figure 5:
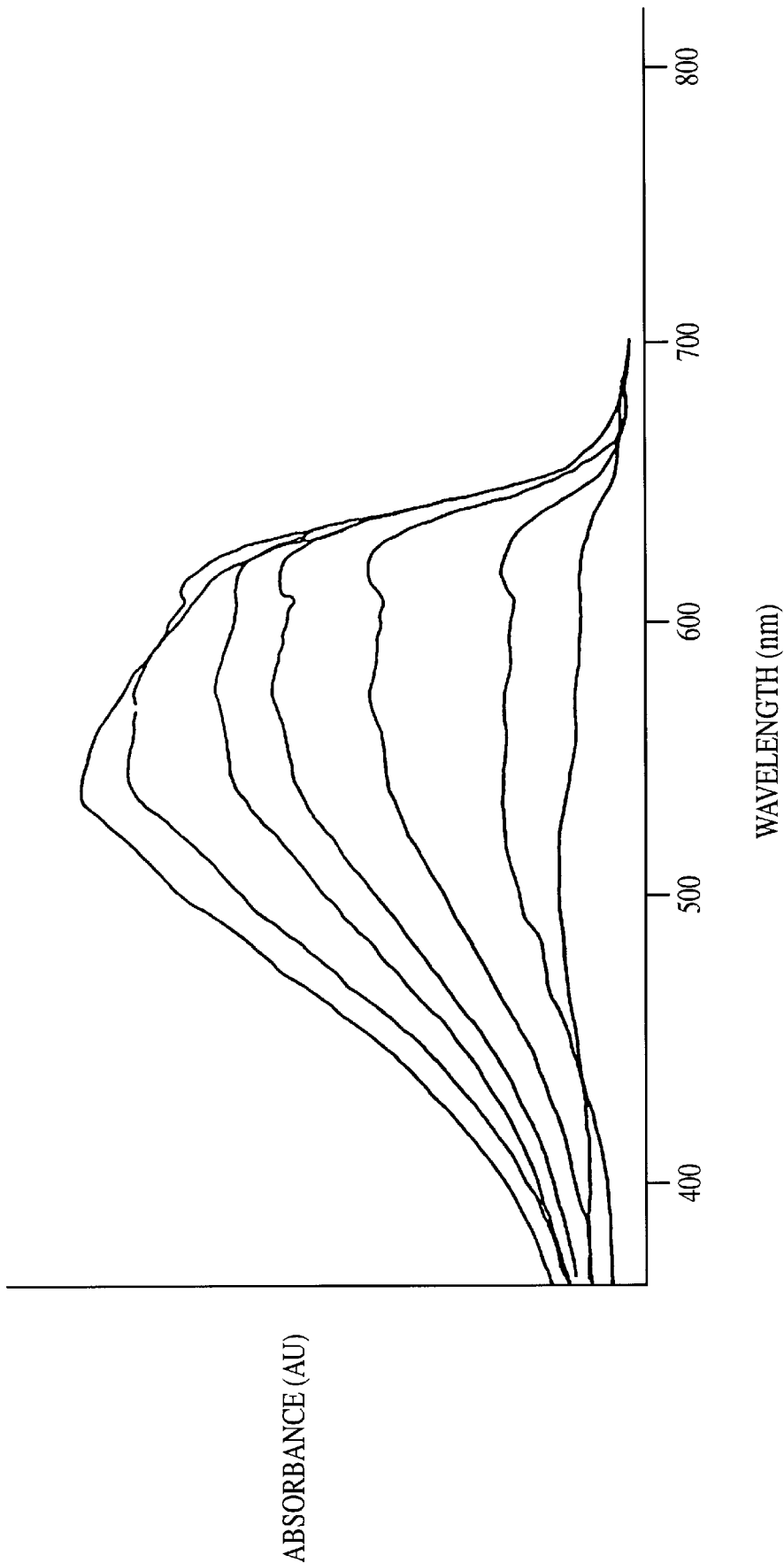
FIG. 5 is a graph of the absorption spectra of a 5% $G_{M1}$ 95% matrix lipid liposomes as a function of UV irradiation time.

The time course of the polymerization is shown in FIG. 5. The visible absorption arises from the conjugated ene-yne system that comprises the polymer backbone. (The monomer absorption occurs at wavelengths less than 300 nm.) The absorption intensity increases with the UV irradiation time and nearly saturates after a total energy dose of 7.2 J/cm$^2$.

The absorption peak at 620 nm is designated as the PDA blue form. The appearance of the colored polymer provides a sensitive and simple test of molecular order in the self-assembled nanostructure. "Looser" structures such as micelles would not form the conjugated polymer due to the topochemical nature of the polymerization reaction. The formation of liposomes in sonicated samples of amphiphilic diacetylenes has been previously demonstrated by electron microscopy. Transmission electron microscopy of the liposomes composed of 5% $G_{M1}$ and 95% 2 indicate an oblong shape with a mean length of 600 nm.

Figure 6A:
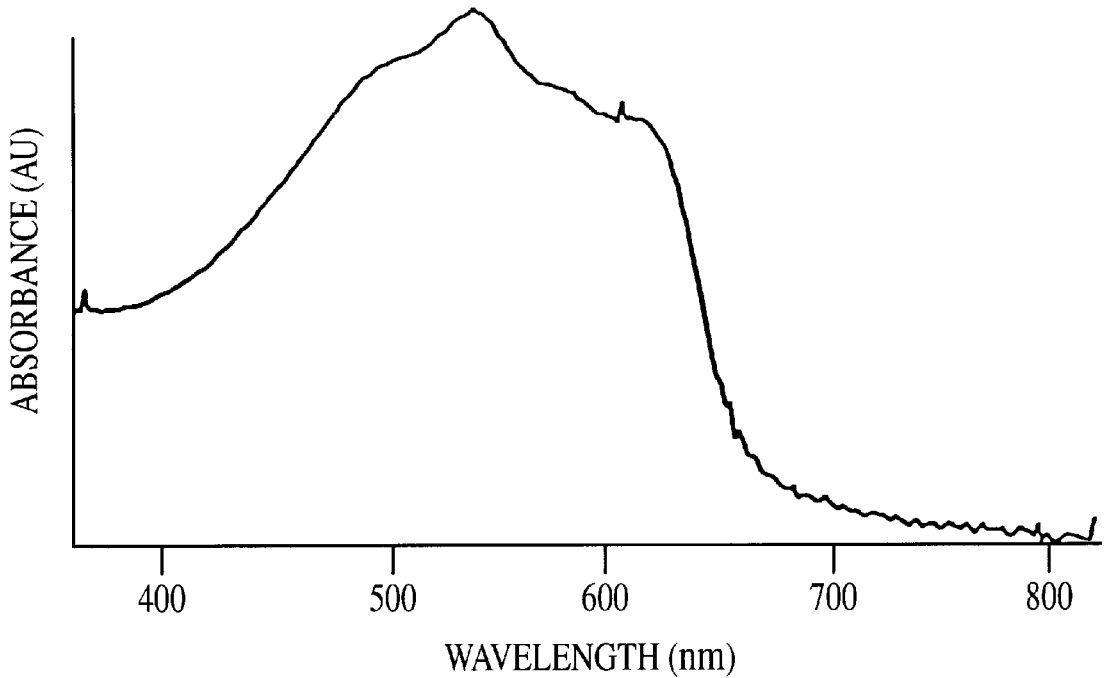
FIGS. 6 A&B are graphs of the absorption spectrum of the inventive liposomes alone and with cholera toxin.
Figure 6B:
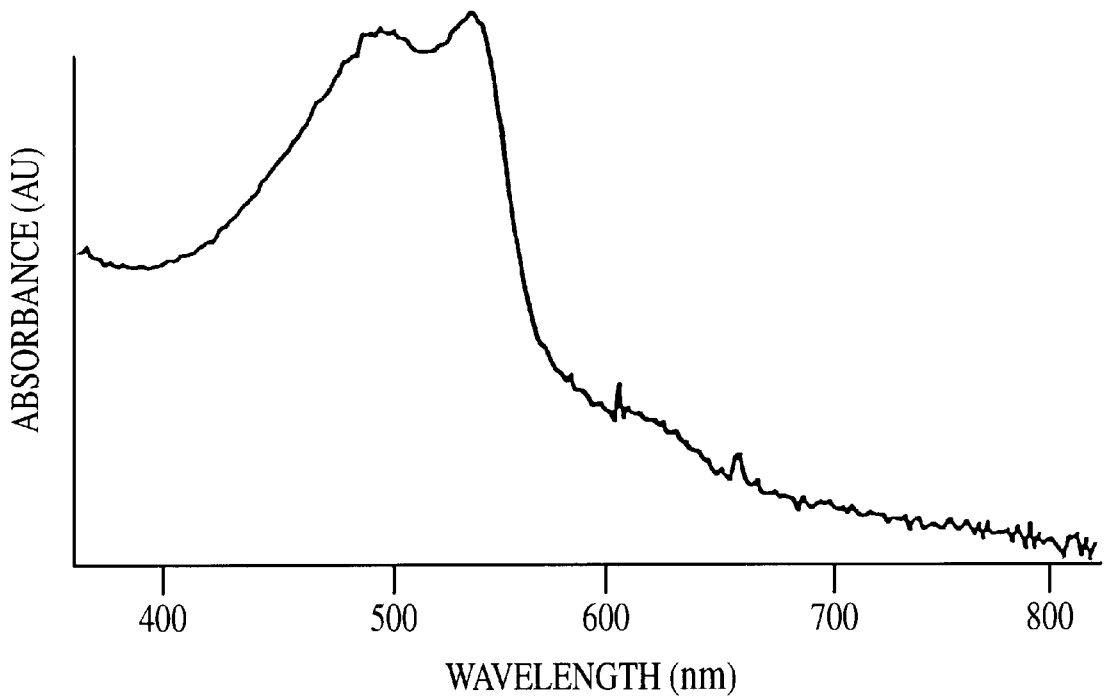

The conjugated ene-yne backbone of poly(diacetylene) liposomes results in the appearance of a deep blue/purple solution. The visible absorption spectrum of the freshly prepared purple liposomes is shown in FIG. 6A. The spectrum can be analyzed by determining the initial percentage of blue phase (%B) in the preparation by comparing the intensity of the peak at 620 nm to the red absorption maxima at 490 nm. Typically, %B≈50 for the initial liposome preparation. When cholera toxin is added to the liposomes composed of 5% $G_{M1}$ and 95% 2, the solution immediately changes to an orange color, and the "red phase" absorption of polydiacetylene dominates, FIG. 6B with %B≈18. The calorimetric response (%CR) is measured as the percent change in the absorption at 620 nm (blue phase polydiacetylene) relative to the total absorption maxima at 620 and 490 nm. A positive response is obtained if the %CR is greater than 7%. These color changes are easily seen with the naked eye, particularly if the liposome solution is placed in a white 96-well microtiter plate. If the ganglioside $G_{M1}$ was mixed with a matrix lipid composed of 10,12 pentacosadiynoic acid instead of 5,7 docosadiynoic acid, (2), the calorimetric response was significantly reduced. The enhanced sensitivity of the system composed of matrix lipid 2 most likely arises from the positioning of the optical reporter group nearer to the interface (three methylene units compared to eight). It has been previously shown by Fourier transform IR spectroscopy that small rotations about the C—C bond b to the polymer backbone are sufficient to change the effective conjugated length. These conformational changes are more easily transduced through shorter alkyl chain length.

A negative response was observed if the ganglioside, $G_{M1}$ ligand was removed from the liposomes (for example, for 233 μg/ml cholera toxin the %CR was ≈6 compared to =43 with the ganglioside present). Similarly, negative responses were obtained when comparable quantities of other proteins besides cholera toxin were added to the $G_{M1}$-containing liposomes. These include, human serum albumin, avidin and wheat germ agglutinin.

Kinetic experiments indicate that greater than 95% of the color change occurs within the first two minutes of adding the toxin. The color transition is not an all or nothing effect but depends on the quantity of toxin titrated into the solution, FIG. 7. The sigmoid behavior suggests cooperativity of the colorimetric transition. This may indicate that the binding itself is cooperative in the sense that binding of toxin to the $G_{M1}$ ligand makes the binding of subsequent toxins more favorable. Alternatively this result might more appropriately be understood in terms of the lipid-polymer side chain conformation and its result on the effective conjugated length of the polydiacetylene backbone. Once the effective conjugated length is reduced as a result of toxin binding, subsequent perturbation of the remainder of the lipid-polymer backbone becomes more favorable. This might be explained as a reduced activation barrier of the blue to red conversion. Temperature-dependent studies of the blue to red transition induced by molecular recognition as well as by heat (thermochromism) may shed light on the relative energetics of the blue-red transition. In addition, the effects of liposome size and $G_{M1}$ mole density on the absolute sensitivity of this approach will be examined.

The inventor has demonstrated that protein-ligand molecular recognition occurs at the interfacial region of polymerized liposomes and that molecular recognition can be directly linked to signal transduction. Such artificial membranes resemble the organization and functionalization of cell membranes but have the added benefit of a built-in synthetic 'trigger' that signals molecular recognition events by an easy to measure color change. Non-specific adsorption if it occurs, does not appear to effect the color of the liposome solutions. These results establish that polymerized supramolecular assemblies offer an alternative approach to investigating molecular recognition at tailored interfaces.

EXAMPLE 1

Cholera Toxin Detection

Ganglioside, $G_{M1}$, cholera toxin from *Vibrio Cholerae*, human serum albumin, and wheat germ agglutinin were purchased from Sigma. 5,7 Docosadiynoic acid was synthesized. Deionized water was obtained by passing distilled water through a Millipore μF ultrapurification train. Solvents used were reagent grade.

Figure 2:
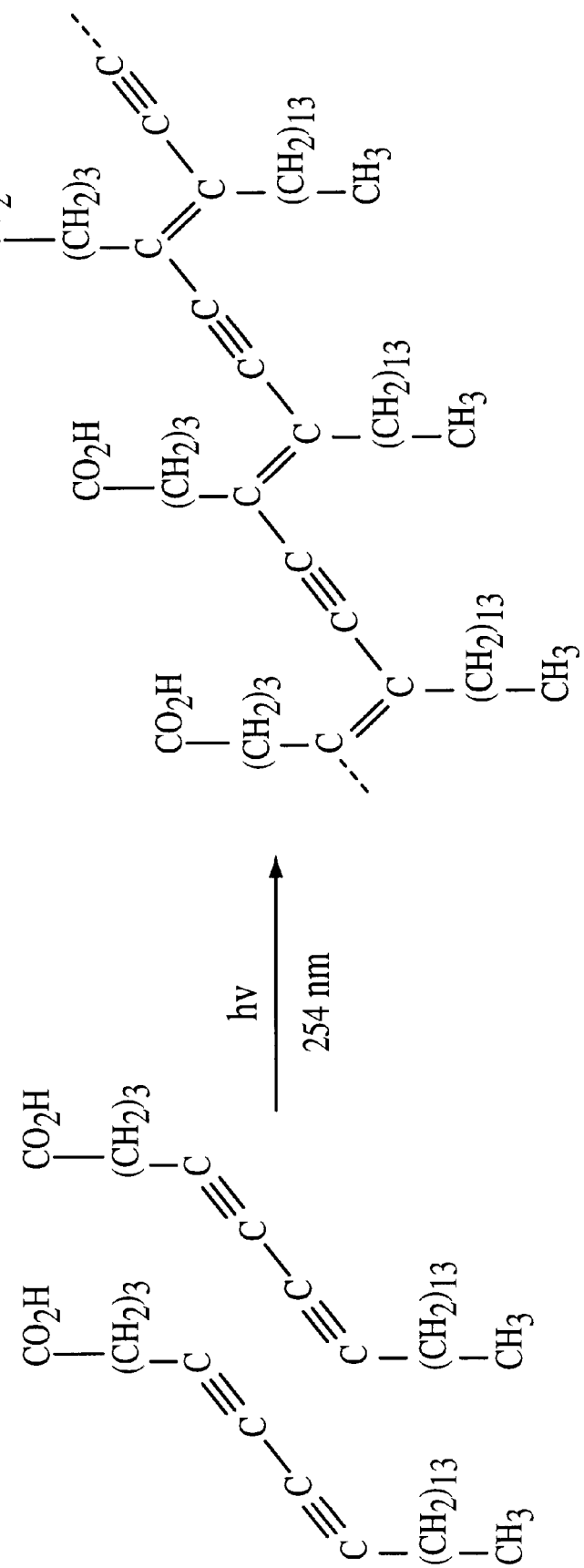
FIG. 2 is a chemical formula representation of the polymerization of 5,7-Docosadiynoic acid monomer into a liposomic polymer.
Figure 3:
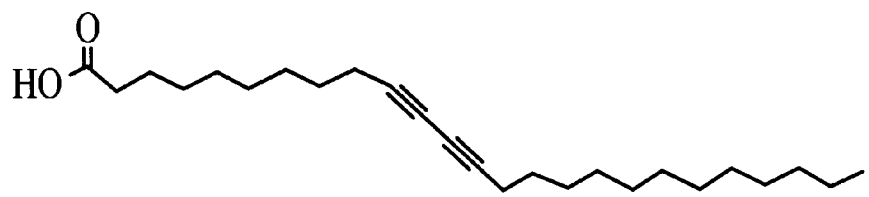
FIG. 3 is a chemical structural representation of some of the variants of the inventive diacetylene monomer structures.
Figure 3:
Figure 3:
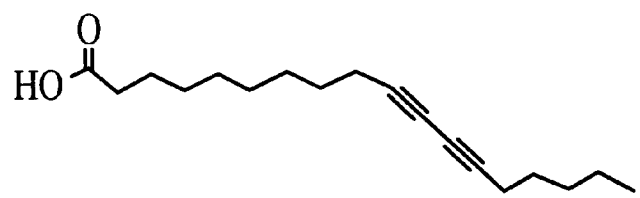
Figure 3:
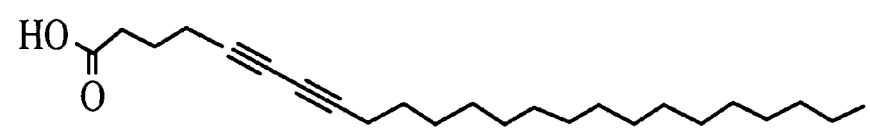
Figure 3:
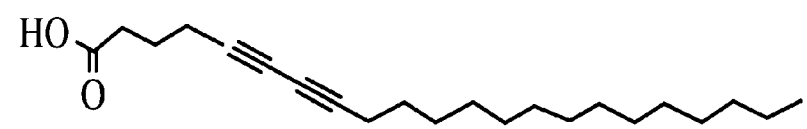
Figure 4:
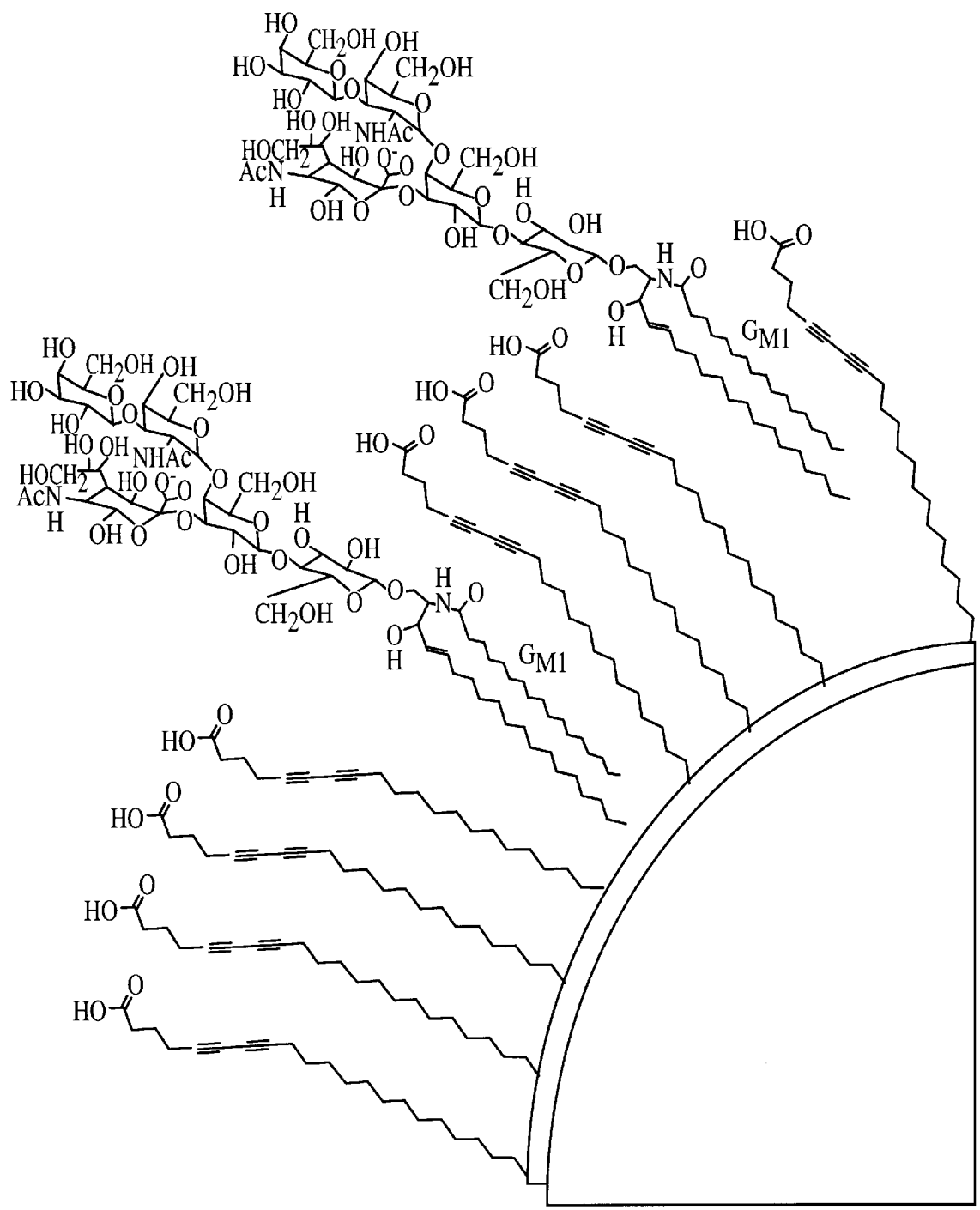
FIG. 4 is a chemical structural representation of $G_{M1}$ assembled with 5,7-Docosadiynoic acid on a liposome.

In the protocol for the formation of the liposomes, compounds 1 and 2 as seen in FIG. 1 were dissolved in methanol and chloroform, respectively. The solutions were mixed in appropriate volumes to achieve a lipid mixture of 5% by mole of $G_{M1}$ and total lipid content of 2 μmol. The solvent was evaporated by rotary evaporation and 2 mL of deionized water added to the dried lipid. The suspension was probe sonicated, cooled, and polymerized for 60 min. using a hand-held UV lamp (254 nm) as shown in FIG. 2. The resulting blue/purple liposome (as shown in FIG. 4) suspension was stored in the dark at 4° C.

For the calorimetric assay, cholera toxin was diluted to 1 mg/mL in 50 mM Tris buffer, pH 7.0. In a 500 μL glass cuvette, blue phase liposomes produced as above were diluted 1:5 in 50 mm Tris buffer, pH 7.0. The liposomes were preincubated in the buffer for 15–30 min to ensure stability of the blue phase prior to the addition of cholera toxin. No color changes were observed during this period.

Cholera toxin was added to the cuvette by the method of successive additions. After each addition, the contents were mixed and the visible absorption spectrum was recorded as a function of time. Typically, 95% of the absorption changes were observed to occur within the first 2 min after addition of toxin. After each experiment, the contents of the cuvette were transferred to a single well of a white microtiter plate. The pink-orange color of the cholera-treated liposomes was verified visually with a blue negative control.

Results

FIG. 5 shows the visible absorption spectra of poly (diacetylene) liposomes composed of 5% $G_{M1}$ ligand, 1, and 95% matrix lipid 2 as a function of UV irradiation time. The liposomes were exposed to a total energy dose of 7.2 J/cm². Each spectrum (in order of increasing absorption) corresponds to a dose of 0.8, 1.6, 2.4, 3.2, 4.0, 5.6, and 7.2 J/cm².

FIG. 6 shows the results of the calorimetric detection of cholera toxin by polymerized diacetylene liposomes (5% $G_{M1}$ and 95% 2). (A) Visible absorption spectrum of blue/purple liposome solution prior to addition of cholera toxin. Liposomes were a diluted in Tris buffer, pH 7.0, to a final concentration of μM total lipid. (B) Visible absorption spectrum of liposomes after the addition of cholera toxin to a final concentration of 310 μG/mL. The incubation time with the liposomes was 2 min.

Figure 7:
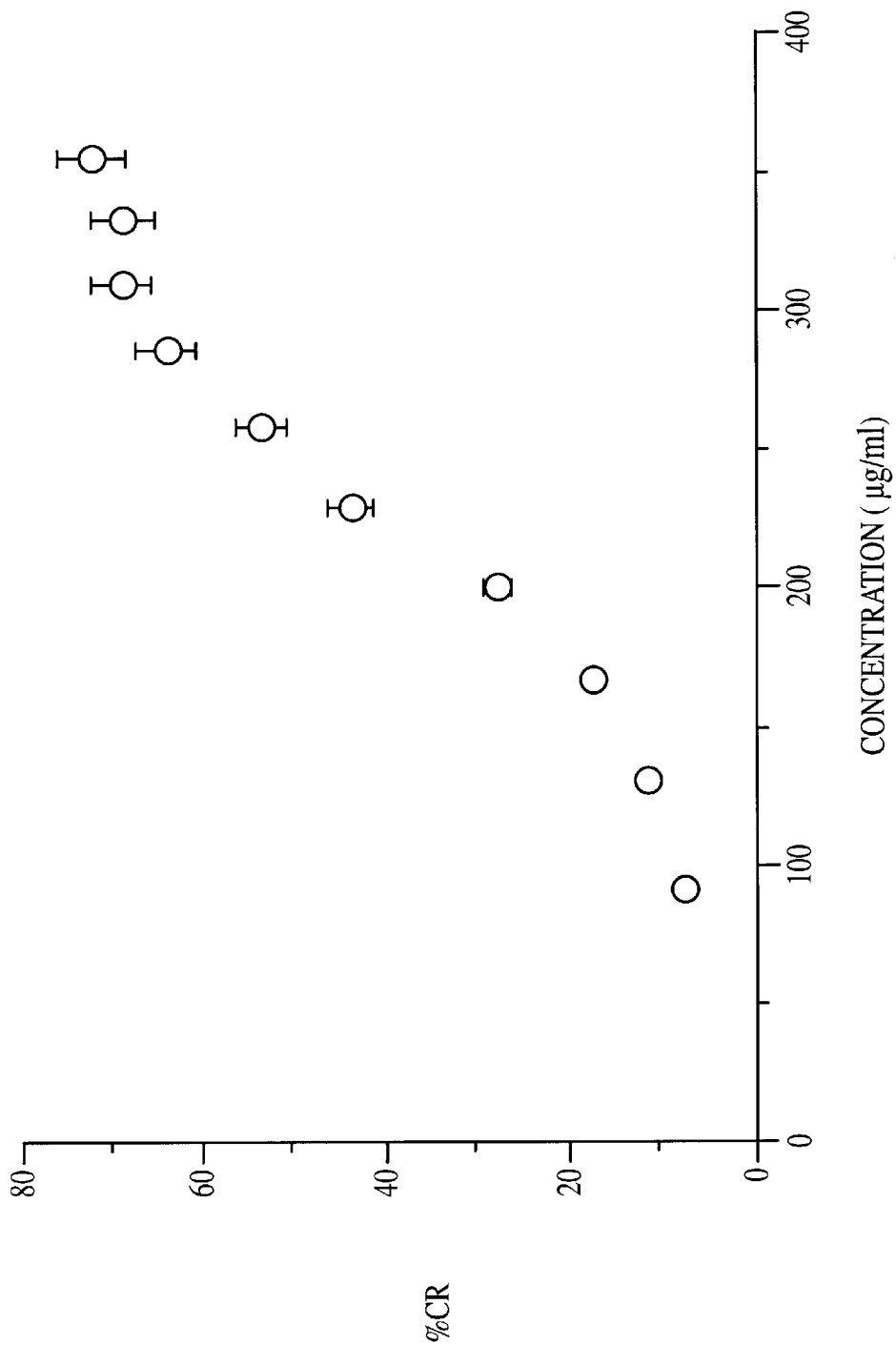
FIG. 7 is a graph of the colorimetric response of polymerized liposomes after successive additions of cholera toxin.

FIG. 7 shows the colorimetric response (%CR) of polymerized liposomes (5% $G_{M1}$ and 95% 2) after successive additions of cholera toxin. The liposomes were incubated with toxin for 2 min after each addition and the spectrum recorded as in FIG. 6.

In order to quantify the response of a liposome solution to a given amount of toxin, the visible absorption spectrum of the liposome solution without the toxin was analyzed as $$B_o = I_{620}/(I_{620}+I_{490})$$

The same value was calculated for liposome solutions exposed to cholera toxin ($B_{ct}$). The calorimetric response (%CR) is defined as the percentage change in B upon exposure to toxin:

$$CR = [B_o - B_{ct}]/B_o \times 100\%$$

EXAMPLE 2

E. coli Toxin Detection

Ganglioside, $G_{M1}$, cholera toxin from *Vibrio Cholera*, human serum albumin, and wheat germ agglutinin were purchased from Sigma. 5, 7 Docosadiynoic acid was synthesized. The formation of the liposomes was accomplished as in Example 1, above, with 5% by mole of $G_{M1}$.

For the colorimetric assay, *E. coli* toxin (Sigma) was spun through a 30 K molecular weight cutoff filter at 2000×g, 15 degree C. to remove salts. The protein was re-diluted in 50 mM Tris buffer pH 7.0 to a final concentration of 1 mg/ml. Controls The liposomes (1 mM) in water was diluted with 50 mM Tris buffer, pH 8.0 to a final concnetration of 0.2 mM. (40 uL of liposomes plus 160 uL of buffer). The absorption spectra of the diluted liposomes was recorded in a plastic cuvette.

Figure 8:
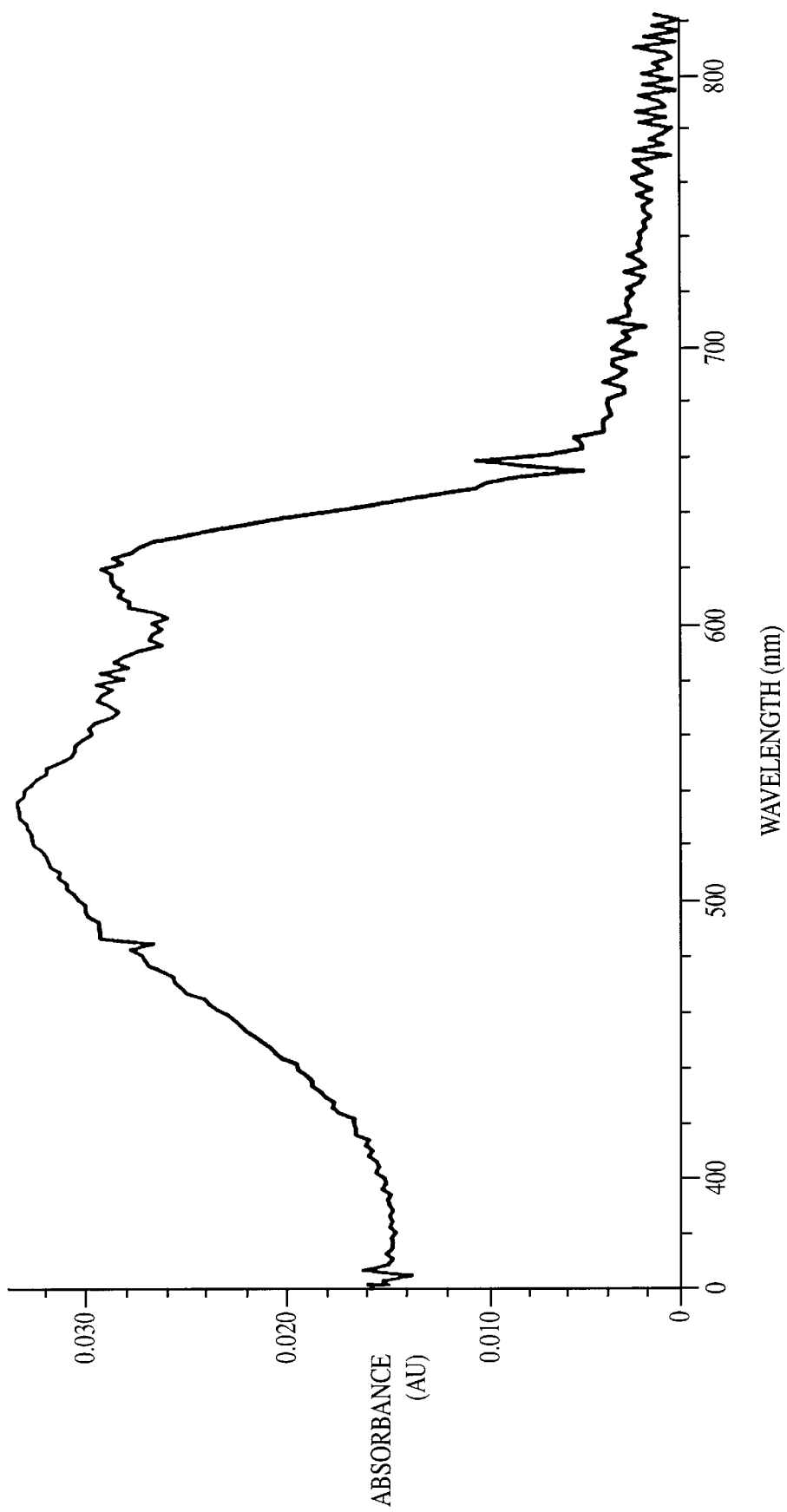
FIG. 8 is a visible absorption spectrum of the polymeric liposomes containing 5% GM1 ligand and 95% 5,7 docosadiynoic acid (DCDA).

FIG. 8 shows the visible absorption spectrum of the polymeric liposomes containing 5% GM1 ligand and 95% 5,7 docadiynoic acid (DCDA). The liposomes were diluted in 50 mM Tris buffer, pH 8.0 to a final concentration of 0.2 mM in a plastic disposable cuvette. The solution in the cuvette appears purple to the naked eye.

*E. coli* toxin

To the liposome solution in the cuvetted, 40 uL of the above *E. coli* toxin was added and the sample allowed to incubate for 10 minutes. The visible absorption spectrum was again recorded, in FIG. 9. The solution in the cuvette appears pink to the naked eye after the addition of the toxin compared to a purple color before the addition. The absorption spectra of FIG. 8 and FIG. 9 confirm the color changes observed.

Figure 9:
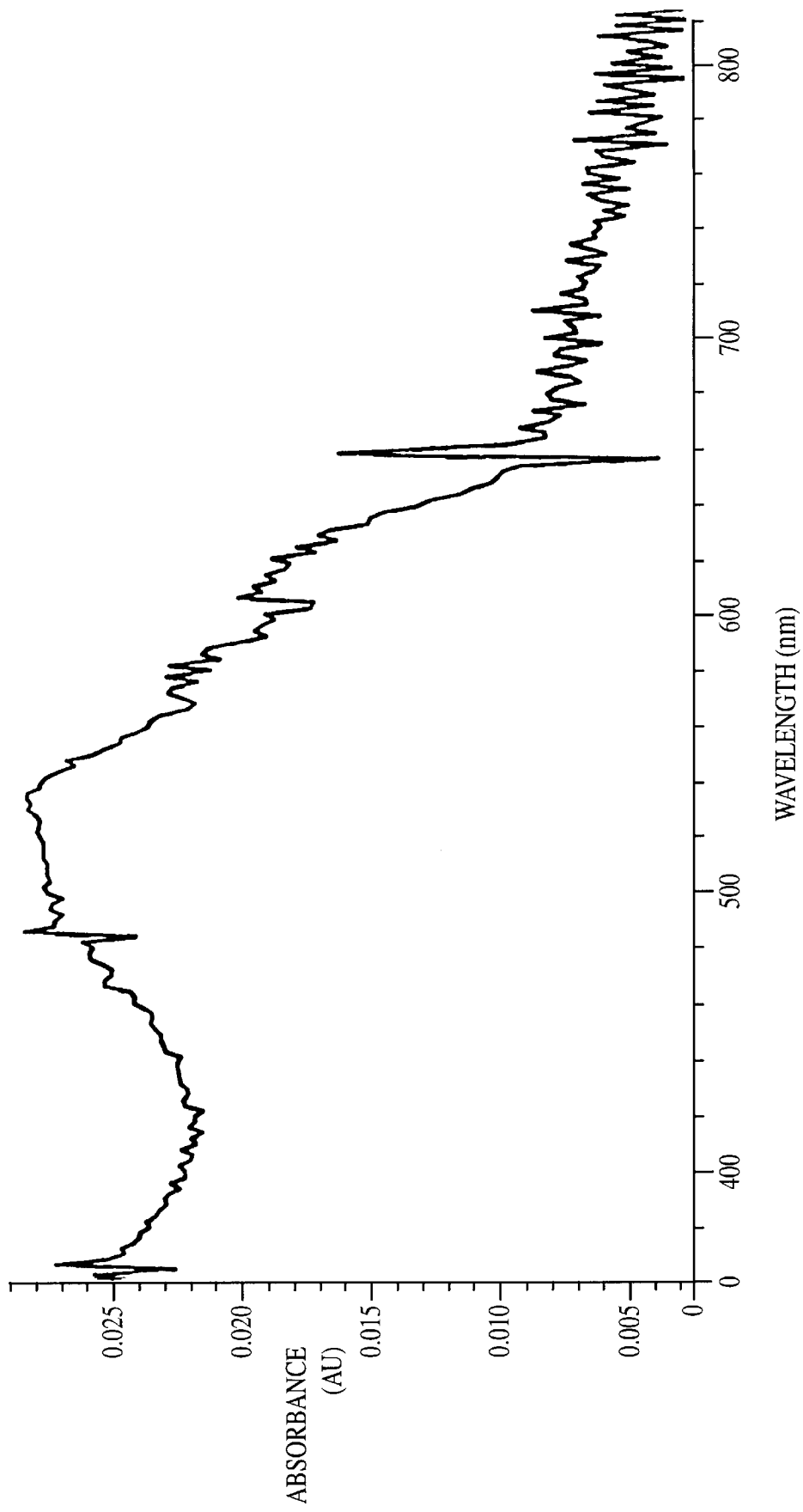
FIG. 9 is the visible absorption of the same polymeric liposomes as in FIG. 8, after the addition of 40 uL of 1 mg/ml E. coli enterotoxin.

FIG. 9 shows the visible absorption of the same polymeric liposomes as in FIG. 8, however after the addition of 40 uL of 1 mg/ml *E. coli* enterotoxin in 50 mM Tris buffer pH 7.0. The spectrum was recorded 10 minutes after exposure to the toxin without stirring. The solution in the cuvette appears 'pink' to the naked eye.

What is claimed is:

1. A composition comprising polymerized liposomes, wherein said polymerized liposomes comprise: i) a plurality of polymerized diacetylene lipid monomers comprising a polymerizable group; and ii) one or more ligands selected from the group consisting of proteins, carbohydrates, nucleic acids, gangliosides, and combinations thereof, wherein said ligands are attached to said liposomes and wherein said liposomes change color upon the binding of one or more analytes to said one or more ligands.

2. The composition of claim 1, wherein said diacetylene lipid monomers comprise hydrophilic head groups, wherein said hydrophilic head groups are attached to said polymerizable group by a chain of 2 to 18 carbons.

3. The composition of claim 2, wherein said hydrophilic head groups are attached to said polymerizable group by a chain of 3 to 10 carbons.

4. The composition of claim 2, wherein said hydrophilic head groups are selected from the group consisting of carboxylic acid, hydroxyl groups, amine groups, amino acid derivatives, and hydrophobic groups.

5. The composition of claim 1, wherein said one or more ligands comprises sialic acid.

6. The composition of claim 1, wherein said one or more ligands is ganglioside $G_{M1}$.

7. The composition of claim 1, wherein said polymerizable group is positioned at the $C_5$ to $C_7$ positions of said lipid monomer.

8. The composition of claim 1, wherein said polymerizable group is positioned at the $C_{10}$ to $C_{12}$ positions of said lipid monomer.

9. The composition of claim 1, wherein said plurality of diacetylene lipid monomers comprise lipid monomers having a chain length of 16 to 25 carbons.

10. The composition of claim 9, wherein said plurality of diacetylene lipid monomers comprise lipid monomers having a chain length of 22 carbons.

11. The composition of claim 1, wherein said diacetylene lipid monomers are selected from the group consisting of 5,7-docosadiynoic acid, 5,7-tetracosadiynoic acid, 10,12-pentacosadiynoic acid, 10-12-tricosadiynoic acid, and 10,12-octadecadiynoic acid.

12. The composition of claim 1, wherein said one or more analytes has a molecular weight of from about 10,000 MW to about 150,000 MW.

13. The composition of claim 1, wherein said one or more analytes is selected from the group consisting of pathogens, enzymes, drugs, toxins and hormones.

14. The composition of claim 13, wherein said pathogens are selected from the group consisting of viruses, bacteria, parasites, and fungi.

15. The composition of claim 13, wherein said toxins are selected from the group consisting of cholera toxin, pertussis toxin, enterotoxin, and toxin A.

16. A method of making polymerized liposomes capable of changing color in the presence of an analyte, comprising:
   a) providing: i) a plurality of diacetylene lipid monomers comprising a polymerizable group; ii) one or more ganglioside ligands upon the binding of one or more analytes to said one or more ganglioside ligands.

17. The method of claim 16, wherein said combining said lipid monomers, said one or more ganglioside ligands, and said one or more organic solvents comprises covalently attaching said ligand to said lipid monomer to produce ligand-linked lipids and dissolving said ligand-linked lipids in said organic solvent to produce said organic mixture.

18. The method of claim 16, wherein said combining said lipid monomers, said one or more ganglioside ligands, and said one or more organic solvents comprises dissolving said lipid monomer in a first organic solvent to produce a first mixture, dissolving said one or more ganglioside ligands in a second organic solvent to produce a second mixture, and mixing said first and said second mixtures to produce said solvent mixture.

19. The method of claim 16, wherein said one or more organic solvents is selected from the group consisting of chloroform, benzene, alcohol, cyclohexane, hexanes, methylene chloride, acetonitrile, carbon tetrachloride, and combinations thereof.

20. The method of claim 16, wherein said aqueous solution is selected from the group consisting of deionized water, buffer solution, physiological saline, phosphate buffered saline, Trizma buffer, (N-2-hydroxyethylpiperazine-N'-2-ethanesulfonic acid), and (3-[N-morpholino] propanesulfonic acid).

21. The method of claim 16, wherein said agitated lipid-ligand mixture in step e) is filtered before cooling in step f).

22. The method of claim 16, wherein said cooling in step f) is conducted at temperatures between 4° C. and −20° C., for a period of time between 5 minutes and 24 hours.

23. The method of claim 16, wherein said cooling in step f) is conducted at temperatures between 0° C. and −15° C., for a period of time between 5 and 20 minutes.

24. The method of claim 16, wherein said cooling in step f) is conducted at temperatures between 0° C. and −5° C., for a period of time between 5 and 12 minutes.

25. The method of claim 16, wherein said polymerizing of said liposomes in step g) is conducted at temperatures between 1° C. and 22° C.

26. The method of claim 16, wherein said polymerizing of said liposomes in step g) is accomplished by ultra-violet irradiation.

27. The method of claim 26, wherein said polymerizing of said liposomes in step g) is accomplished with an energy dose of from about 0.10 joules/cm$^2$ to 10 joules/cm$^2$.

28. The method of claim 16, wherein said polymerizing of said liposomes in step g) is accomplished by a polymerization means selected from the group consisting of gamma radiation, electron beam, and X-rays.

29. The method of claim 16, wherein said lipid monomers comprise hydrophilic head groups, wherein said hydrophilic head groups are attached to said polymerizable groups by a chain of 2 to 18 carbons.

30. The method of claim 29, wherein said hydrophilic head groups are attached to said polymerizable groups by a chain of 3 to 10 carbons.

31. The method of claim 30, wherein said hydrophilic head groups are selected from the group consisting of carboxylic acid, hydroxyl groups, amine groups, and amino acid derivatives.

32. The method of claim 16, wherein said one or more ganglioside ligands comprises ganglioside $G_{M1}$.

33. The method of claim 16, wherein said polymerizable group is positioned at the $C_5$, $C_6$ or $C_7$ positions of said lipid monomer.

34. The method of claim 16, wherein said polymerizable group is positioned at the $C_{10}$, $C_{11}$ or $C_{12}$ positions of said lipid monomer.

35. The composition of claim 16, wherein said plurality of diacetylene lipid monomers comprise lipid monomers having a chain length of 16 to 25 carbons.

36. The composition of claim 35, wherein said plurality of diacetylene lipid monomers comprise lipid monomers having a chain length of 22 carbons.

37. The method of claim 16, wherein said diacetylene lipid monomers are selected from the group consisting of 5,7-docosadiynoic acid, 5,7-tetracosadiynoic acid, 10,12-pentacosadiynoic acid, 10-12-tricosadiynoic acid, and 10,12-octadecadiynoic acid.

38. A composition comprising polymerized liposomes, wherein said polymerized liposomes comprise: i) a plurality of polymerized 5,7-docosadiynoic acid lipid monomers; and ii) one or more ligands, wherein said ligands are gangliosides, wherein said ligands are attached to said liposomes and wherein said liposomes change color upon the binding of one or more analytes to said one or more ligands.

39. A composition comprising polymerized liposomes capable of changing color in the presence of an analyte made by the method of claim 16.

* * * * *